United States Patent [19]

Kwiatek et al.

[11] 3,946,067

[45] Mar. 23, 1976

[54] PROCESS FOR THE PREPARATION OF AROMATIC ALDEHYDES

[75] Inventors: Jack Kwiatek; Jawad H. Murib, both of Cincinnati, Ohio; Charles K. Brush, Minneapolis, Minn.

[73] Assignee: National Distillers and Chemical Corporation, New York, N.Y.

[22] Filed: Jan. 28, 1975

[21] Appl. No.: 544,613

Related U.S. Application Data

[63] Continuation of Ser. No. 284,524, Aug. 29, 1972, abandoned.

[52] U.S. Cl.......... 260/476 R; 260/599; 260/600 R; 260/515 R; 260/592
[51] Int. Cl.².................. C07C 67/30; C07C 45/02
[58] Field of Search............ 260/599, 600 R, 476 R, 260/515 R, 592

[56] References Cited
UNITED STATES PATENTS 3,162,683  12/1964  Jones et al. ........................ 260/524

3,488,395  1/1970  Hooper .............................. 260/599

FOREIGN PATENTS OR APPLICATIONS 408,184  9/1920  Germany ........................... 260/599

*Primary Examiner*—Bernard Helfin
*Attorney, Agent, or Firm*—Kenneth D. Tremain

[57] ABSTRACT

A process is described for the preparation of aromatic aldehydes such as benzaldehyde or substituted benzaldehydes involving the vapor phase oxidation of aralkyl compounds such as toluene or substituted toluenes, respectively, at temperatures of less than about 250°C. in the presence of a catalyst composition containing phosphoric acid and a catalytically effective amount of palladium metal. The aromatic aldehydes are produced in a single reaction step.

15 Claims, No Drawings

PROCESS FOR THE PREPARATION OF AROMATIC ALDEHYDES

This is a continuation of application Ser. No. 284,524 filed Aug. 29, 1972, and now abandoned.

BACKGROUND OF THE INVENTION

The present invention relates to a process for the preparation of aromatic aldehydes by the catalytic oxidation of aralkyl organic compounds such as toluene or substituted toluenes, preferably in the vapor phase. More particularly, the invention pertains to the reaction or aralkyl compounds with molecular oxygen in the presence of a supported catalyst containing phosphoric acid and palladium metal. The vapor phase process of the invention can be effectively employed, for example, the preparation of benzaldehyde from toluene.

Current industrial practice for the oxidation of toluene to benzaldehyde utilizes a uranium oxide/molybdenum oxide catalyst at about 500°C. (W. L. Faith, D. B. Keyes and R. L. Clark, Industrial Chemicals, 3rd Ed., John Wiley & Sons, Inc., New York, 1965). It is among the objects of the present invention to provide a novel process for the selective production of aromatic aldehydes such as benzaldehyde or substituted benzaldehydes at relatively low temperatures.

SUMMARY OF THE INVENTION

In accordance with the present invention an aralkyl compound such as toluene or a substituted toluene is oxidized, preferably in the vapor phase, by molecular oxygen at temperatures of less than about 250°C. in the presence of a catalyst composition containing phosphoric acid and a catalytically effective amount of palladium metal to form the desired aromatic aldehyde. The process employs a heterogeneous catalyst contact system; e.g., a system consisting of a fixed, moving or fluidized catalyst bed. The following equations are illustrative of the reactions which may be carried out by employing the process of this invention:

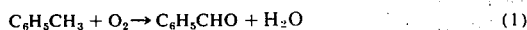

$$C_6H_5CH_3 + O_2 \rightarrow C_6H_5CHO + H_2O \qquad (1)$$

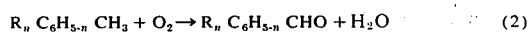

$$R_n C_6H_{5-n} CH_3 + O_2 \rightarrow R_n C_6H_{5-n} CHO + H_2O \qquad (2)$$

wherein R is an alkyl radical having from 1 to 6 carbon atoms, an aryl group having at least 4 carbon atoms, an alkoxy or aryloxy radical having from 1 to 7 carbon atoms, a carboxyl radical having from 1 to 8 carbon atoms, or mixture thereof, and wherein n ranges from 0 to 5.

Illustrative aralkyl compounds are as follows:
1. Arenes having from 7 to 17 carbon atoms such as:
Toluene
o-Xylene
m-Xylene
p-Xylene
p-Cymene
Mesitylene
Durene
Pentamethylbenzene
Hexamethylbenzene
Methylnapthalene
p-Phenyltoluene
2,2-di(p-tolyl) propane, etc.
2. Alkoxy and aryloxy substituted toluenes having from 8 to 14 carbon atoms such as:
m-Methoxytoluene
o-Methoxytoluene
p-Methoxytoluene
p-Phenoxytoluene
Ditolyl ether
2,5-Dimethoxytoluene, etc.
3. Carbonyl and carboxyl substituted toluenes having 8 to 15 carbon atoms such as:
Methyl p-toluate
p-Methyl benzoic acid
p-Methylbenzophenone
4-Methylphthalic anhydride, etc.

In general the preferred organic feed material will be aromatic organic compounds containing a tolyl radical, i.e., $CH_3C_6H_4$-, such as toluene, o-xylene, m-xylene, p-xylene, durene, mesitylene, and the like.

Carrying out the reaction in the gas phase is a relatively simple and efficient operation, permitting the use of a continuous process, and thus is commercially attractive. It has been found that use of the indicated procedure results in the selective formation of benzaldehyde or a substituted benzaldehyde at relatively low temperatures.

The following description of preferred forms of the invention relates principally to the oxidation of toluene to benzaldehyde. It will, however, be understood that the process described herein is similarly applicable to the oxidation of aralkyl organic compounds as set forth in equation (2) hereinabove, and that such latter embodiment is, therefore, also embraced within the scope of the present invention. It is also possible, and within the scope of the invention, to prepare a di-aldehyde, e.g., p-terephthalaldehyde from p-xylene.

DESCRIPTION OF THE PREFERRED EMBODIMENTS

Toluene, the preferred organic feed material, reacted in the present process may be fed in pure form or, alternatively, may be impure in the sense that it may contain diluents, such as, e.g., up to about 50 mole percent thereof of inert hydrocarbons such as heptane, cyclohexane or benzene. The oxygen feed may similarly be pure oxygen or, alternatively, an oxygen-containing gas mixture such as air or air enriched with oxygen. In addition to these materials, the gaseous feed mixture employed in the process contains water vapor and may contain other inert diluents such as nitrogen or carbon dioxide.

The gaseous mixture of such reactants is contacted with a catalyst composition comprising phosphoric acid and a catalytically effective amount of palladium metal suitably supported on a conventional catalyst carrier such as, for example, carbon, silica, alumina, titania, carborundum, an ion-exchange resin, or the like.

The support is impregnated or loaded with the phosphoric acid, and the palladium metal, whether alone or admixed, alloyed, or in solid solution with a Group IB or Group VIII is deposited thereon. Such other metals include gold, silver, platinum, rhodium, ruthenium, iridium, and the like as well as mixtures thereof. As indicated below, the catalytically effective palladium metal and the phosphoric acid may be deposited on or impregnated in the catalyst carrier in any desired sequence, the combined supported catalyst composition, however formed, being active in the present process. The phosphoric acid may also be added continuously to the reaction mixture in the form of an aqueous solution to maintain a trickle liquid phase over the catalyst bed.

In this case, the phosphoric acid in the effluent mixture may be recovered and recycled.

The palladium metal is incorporated in amounts of from about 0.1 to 5%, preferably from about 0.5 to 3.0%, by weight of the metal and carrier. The phosphoric acid is incorporated in amounts of at least 1%, and up to as much as about 50%, preferably from about 5 to 30%, by weight of the total catalyst composition. If another metal, e.g., gold, is present in the catalyst composition it will be incorporated in an amount ranging from about 1 to 200, preferably from about 10 to 75%, by weight based on the weight of the palladium.

It has been found, in accordance with the present invention, that palladium-containing compositions which do not incorporate either phosphoric acid or other strong inert acids such as phosphosilicic acid, are not useful in the process. Furthermore, catalyst compositions such as palladium-gold-phosphoric acid or palladium-platinum-phosphoric acid are active, and may exhibit improved stability characteristics compared to palladium-phosphoric acid catalysts.

Deposition of the catalytically effective amount of palladium metal utilized in this process may be effected by conventional techniques, such as by contacting the catalyst support with a solution of a suitable palladium salt or complex, e.g., palladium chloride, palladium acetate, palladium nitrate or palladium acetylacetonate, and thereafter reducing the palladium compound to the metal with hydrogen or other appropriate reducing agents. Alternatively, the salt may, if desired, be reacted with alkali to form the corresponding palladium oxide, and the latter may thereafter be reduced to the catalytically active metal.

When the palladium metal is deposited prior to impregnation of the support with phosphoric acid the palladium salt may be applied from either aqueous or organic media, e.g., water or organic solvents such as lower alkanols, e.g., methanol or ethanol, benzene, chloroform, or the like. When, on the other hand, the palladium metal is deposited after impregnation with phosphoric acid, the palladium salt is usually applied from an organic solvent. Organic media are preferred in this alternative embodiment inasmuch as the presence of water may tend to remove a portion of the phosphoric acid from the carrier. Alternatively, palladium salts may be simultaneously applied with phosphoric acid from compatible solvents.

The catalyst carrier, with or without palladium incorporation, may be loaded with phosphoric acid by impregnating the support either with syrupy phosphoric acid, e.g., 85% $H_3PO_4$, or with more dilute aqueous solutions of phosphoric acid. The carrier may then be used as such, or alternatively, it may be subsequently dried either in a stream of hot air or in a vacuum oven.

Commercially available catalyst materials may be utilized in the preparation of the catalyst compositions hereof. Thus, for example, either a commercial supported palladium metal catalyst may be treated with phosphoric acid, or a commercial supported phosphoric acid catalyst may have palladium metal deposited thereon, to form catalyst compositions useful herein.

It has been found desirable in accordance with the present invention to additionally incorporate a protic solvent, such as water, in the reaction mixture. Whether such material acts as a catalyst promoter or otherwise participates in a complex reaction with the substrate is not presently understood. While such material is, for purposes of convenience, referred to hereinafter as a catalyst promoter, it will be understood that its use in the process is contemplated, irrespective of the actual mechanism by which it may act.

The water may, for example, be added as a vapor to the gaseous feed mixture by bubbling the oxygen-containing gas stream through liquid water. Alternatively, water may be separately vaporized and metered into the reaction zone. If desired, in lieu of the preferred vapor phase operation of this invention, the water may be added continuously with phosphoric acid to maintain a mixed phase, i.e., a trickle liquid phase, over the catalyst bed.

While stoichiometric proportions of the toluene and oxygen reactants, viz., 1.0 mole of oxygen per mole of toluene, may be utilized in the vapor phase process hereof, it is rather preferred to use reaction mixtures in which oxygen is incorporated in amounts of from about 1 to 50 mole percent, in admixture with from about 1 to 25 mole percent of the toluene, and from about 1 up to about 80, and desirably 5 to 70 mole percent of water vapor promoter. The balance of the reactant mixture consists of hydrocarbons and/or gases inert to the oxidation process.

The vapor phase reaction is carried out at temperatures markedly lower than those which have, heretofore, been generally regarded as necessary for vapor phase toluene oxidation reactions. It has been found that the desired benzaldehyde is selectively formed at reaction temperatures of from about 100° to 250°C., and preferably, from about 140° to 225°C.

The oxidation process may be conducted either at atmospheric or elevated pressures, e.g., up to about 75 psi.

After the gaseous reaction mixture contacts the catalyst composition, the exhaust gases are cooled to condense the oxidation products. The desired benzaldehyde is then separated by any convenient means such as distillation and/or extraction and the like. Benzoic acid is a valuable by-product. Unreacted feed material separated from the recovered effluent may be recycled for further reaction.

The following examples are directed to illustrative embodiments of the vapor phase process hereof, and should not be construed in a limiting sense. As employed herein, yields, conversions and selectivities are defined as follows:

$$\text{Conversion, \%} = \frac{\text{No. of moles feed toluene consumed} \times 100}{\text{No. of moles feed toluene}}$$

$$\text{Selectivity, \%} = \frac{\text{No. of moles benzaldehyde formed} \times 100}{\text{No. of moles feed toluene consumed}}$$

$$\text{Yield, \%} = \frac{\text{No. of moles product formed} \times 100}{\text{No. of moles feed toluene}}$$

The proportions of palladium metal and phosphoric acid in the catalyst compositions described above or set forth in the examples are given as percentages of the total weight of the catalyst compositions, including both the support and the phosphoric acid and palladium metal components thereof, unless otherwise specified.

EXAMPLE 1

A pyrex glass tube reactor (50 cm. × 2.5 cm. OD) is loaded with 12. ml. (volume) of catalyst. The catalyst is prepared by treating 30 grams of 3% palladium supported on carbon with 10 grams of phosphoric acid dissolved in 20 ml. of water, followed by heating in an open, rotating evaporation dish with a heat gun delivering hot air at 125°C.

The reactor is heated to, and maintained at, 140°, when a stream of 300 mmoles/hr. nitrogen, 100 mmoles/hr. oxygen, 180 mmoles/hr. water and 17 mmoles/hr. toluene is passed through the catalyst bed. The exhaust gases are passed through a trap cooled by dry ice, followed by a carbon dioxide absorbing solution. Gas chromatographic and titrimetric analyses on the product of a 5 hour operation indicate product yields of 2.6 mole % benzaldehyde, 0.6 mole % benzoic acid and 0.8 mole % toluene converted to carbon dioxide. The conversion is 4.0% with a benzaldehyde selectivity of 65%.

EXAMPLE 2

A. The procedure described in Example 1 is followed, except that 1.3% palladium/0.6% gold supported on carbon catalyst loaded with phosphoric acid (25% by weight) was employed in a 2 hour run at 165°C. with a stream of 380 mmoles/hr. nitrogen, 100 mmoles/hr. oxygen, 180 mmoles/hr. water and 17 mmoles/hr. toluene. Product yields were 2.8 mole % benzaldehyde, 0.2 mole % benzoic acid, 0.2 mole % benzene and 0.4 mole % toluene converted to carbon dioxide; conversion, 3.6%; benzaldehyde selectivity, 77%.

B. The procedure described in Example 2 (A) is followed, but the palladium-gold-on-carbon catalyst is not loaded with phosphoric acid. Only a trace of benzaldehyde was produced.

EXAMPLE 3

The catalyst described in Example 2 (A) is employed in a five hour run at 180°C. with a stream of 270 mmoles/hr. nitrogen, 85 mmoles/hr. oxygen, 180 mmoles/hr. water and 17 mmoles/hr. toluene. Product yields were 2.8 mole % benzaldehyde, 2.6 mole % benzoic acid, 0.1 mole % benzene and 1.2 mole % toluene converted to carbon dioxide.

EXAMPLE 4

A 1.3% palladium/0.67% gold supported on silica catalyst loaded with phosphoric acid (25% by weight) was employed in a 1 hour run at 155°C. with a stream of 270 mmoles/hr. nitrogen, 100 mmoles/hr. oxygen, 180 mmoles/hr. water and 17 mmoles/hr. toluene. Product yields were 5.7 mole % benzaldehyde, 1.2 mole % benzoic acid, 0.7 mole % toluene converted to carbon dioxide and 0.1 mole % benzyltoluenes (methyldiphenylmethanes); conversion, 7.7%; benzaldehyde selectivity, 74%.

EXAMPLE 5

A. A 1% palladium/0.5% gold on carbon catalyst loaded with phosphoric acid (25% by weight) was employed in a run at 160° and an operating pressure of 50 psi with a stream of 70 mmoles/hr. nitrogen, 20 mmoles/hr. oxygen, 440 mmoles/hr. water and 100 mmoles/hr. toluene. Conversion was 3.9% with a selectivity of 79%.

B. The above catalyst and reaction conditions, except that the temperature was raised to 180°, gave a conversion of 7.3% with a selectivity of 50%.

C. A 1% palladium on silica catalyst loaded with phosphoric acid (25% by weight) was employed in a run at 200° and an operating pressure of 50 psi with essentially the reactant stream described in section (A). Conversion was 3.7% with a selectivity of 55%.

EXAMPLE 6

The procedure described in Example 2 (A), except that o-xylene is oxidized in place of toluene to produce o-tolualdehyde.

EXAMPLE 7

The procedure described in Example 2 (A), except that p-xylene is oxidized in place of toluene to produce p-tolualdehyde.

EXAMPLE 8

The procedure described in Example 2 (A) except that p-cymene is oxidized in place of toluene to produce p-isopropylbenzaldehyde.

EXAMPLE 9

The procedure described in Example 2 (A) except that m-methoxytoluene (m-methylanisole) is oxidized in place of toluene to produce m-methoxybenzaldehyde.

EXAMPLE 10

The procedure described in Example 2 (A), except that methyl p-toluate is oxidized in place of toluene to produce p-carbomethoxybenzaldehyde.

The above data show that without the use of phosphoric acid in the catalyst composition the oxidation process yields little, if any, aldehyde product. The data further show that aromatic aldehydes may be produced in a highly selective manner, and that a variety of substituted toluenes may be employed in the process.

While particular embodiments of this invention are shown above, it will be understood that the invention is obviously subject to variations and modifications without departing from its broader aspects. Thus, while the conversion of toluene to benzaldehyde has been described above in great detail it will be understood that substituted toluenes, i.e., compounds containing the tolyl radical, $CH_3C_6H_4-$, or a substituted tolyl radical, may also effectively be employed as starting materials to produce the corresponding aromatic aldehydes.

What is claimed is:

1. A process for the preparation of aromatic aldehydes which consists essentially of oxidizing in the vapor phase an organic compound selected from the group consisting of toluene, xylene, p-cymene, mesitylene, durene, pentamethylbenzene, hexamethylbenzene, methylnaphthalene, p-phenyltoluene, 2,2-di(p-tolyl) propane, methoxytoluene, p-phenoxytoluene, ditolyl ether, 2,5-dimethoxytoluene, methyl p-toluate, p-methyl benzoic acid, p-methylbenzophenone, and 4-methylphthalic anhydride, with molecular oxygen at a temperature of from about 100°–250°C. in the presence of a supported catalyst composition, said catalyst composition being supported on an inert carrier material having about 1–50 percent by weight of phosphoric acid impregnated therein and about 0.1–5 percent by weight of palladium in the form of palladium metal or palladium metal admixed, alloyed or in solid solution with about 1–200 percent based on the palladium of a Group IB or VIII metal selected from the group consisting of gold, platinum, silver, rhodium, ruthenium and iridium deposited thereon.

2. The process of claim 1 wherein m-methylanisole is oxidized to produce m-methoxybenzaldehyde.

3. The process of claim 1 wherein methyl p-toluate is oxidized to produce p-carbomethoxybenzaldehyde.

4. The process of claim 1 wherein p-cymene is oxidized to produce p-isopropylbenzaldehyde.

5. The process of claim 1 wherein the inert carrier material is carbon.

6. The process of claim 1 wherein the inert carrier material is silica.

7. The process of claim 1 wherein the reaction is carried out at a temperature ranging from about 140° to 225°C.

8. The process of claim 1 wherein the reaction mixture of the organic compound and the molecular oxygen includes water in an amount of up to 80 mole % thereof.

9. The process of claim 1 wherein toluene is oxidized to prepare benzaldehyde.

10. The process of claim 1 wherein xylene is oxidized to produce tolualdehyde.

11. The process of claim 1 wherein the Group IB metal is gold.

12. A vapor phase process for the preparation of benzaldehyde which comprises reacting a gaseous mixture consisting essentially of toluene, molecular oxygen and water vapor at a temperature of from about 100° to 250° C. in the presence of a supported catalyst composition, said catalyst composition being supported on an inert carrier material having about 5 to 30% by weight of phosphoric acid impregnated therein and about 0.5 to 3% by weight of palladium in the form of palladium metal or palladium metal admixed, alloyed or in solid solution with about 1–200 weight percent based on the palladium of a Group IB or Group VIII metal selected from the group consisting of gold, platinum, slver, rhodium, ruthenium and iridium deposited thereon.

13. The process of claim 12 wherein the Group IB metal is gold.

14. The process of claim 12 wherein the inert carrier is carbon.

15. The process of claim 12 wherein the inert carrier is silica.

* * * * *